United States Patent [19]

Gentelia et al.

[11] Patent Number: 4,723,949
[45] Date of Patent: Feb. 9, 1988

[54] FILLING DEVICE AND CAP FOR UNDERWATER DRAINAGE DEVICE

[75] Inventors: John S. Gentelia, Madison; Stephen J. Roberts, Sauquoit, both of N.Y.

[73] Assignee: ConMed, Inc., Utica, N.Y.

[21] Appl. No.: 906,957

[22] Filed: Sep. 15, 1986

[51] Int. Cl.$^4$ ............................................... A61M 1/00
[52] U.S. Cl. .................................................... 604/321
[58] Field of Search ................ 137/205; 141/104, 248; 604/319–321, 119

[56] References Cited

U.S. PATENT DOCUMENTS 3,363,627  1/1968  Bidwell et al. ...................... 604/321
4,354,493  10/1982  Kayser et al. ....................... 604/321

FOREIGN PATENT DOCUMENTS 8403838  10/1984  PCT Int'l Appl. ................ 604/321

Primary Examiner—C. Fred Rosenbaum
Assistant Examiner—J. L. Kruter
Attorney, Agent, or Firm—Larson and Taylor

[57] ABSTRACT

A method and apparatus for filling an underwater drainage device is provided with a rotatable funnel and cap which is positioned between the manometer chamber and water seal chamber in a pleural drainage device. In use the cap may be removed and the funnel positioned to fill the manometer chamber to the desired level and the funnel may then be rotated to fill the underwater seal chamber to the desired level. A positive pressure relief valve is provided in the cap.

8 Claims, 3 Drawing Figures

1

FILLING DEVICE AND CAP FOR UNDERWATER DRAINAGE DEVICE

FIELD OF THE INVENTION

The present invention relates generally to pleural drainage devices and more specifically to a method and apparatus for filling the manometer and underwater seal chambers of pleural drainage devices.

BACKGROUND OF THE INVENTION

It is well known in the prior art to provide a pleural drainage apparatus which incorporates three chambers, namely, a collection chamber, an underwater seal chamber and a manometer chamber. Early patents disclosing such devices are U.S. Pat. Nos. 3,363,626 and 3,363,627. The apparatus shown in such patents incorporates an integrally formed device and incorporates a large collection chamber for collecting fluids drained from the pleural cavity through a thoracotomy tube, a second chamber connected to the collection chamber which protects the pleural cavity from being subject to atmospheric pressure and known as an underwater seal chamber and a third chamber connected to the underwater seal chamber and known as a pressure manometer chamber which serves to regulate the degree of negative pressure within the pleural cavity. This type of apparatus has been highly successful in both removing fluids from the pleural cavity and in maintaining the desired degree of negativity within the pleural cavity.

It will be noted that in such well known prior art devices both the pressure manometer chamber and underwater seal chamber must be prefilled with liquid such as water prior to use of the device. It is essential that the correct amount of water be put in these chambers as any excess in the amount of water or failure to fill the chambers to the correct level can result in improper operation of the device and inability to maintain the proper degree of negativity within the pleural cavity. Thus, there has been a clear need in the prior art for a mechanism which will permit a safe, fast filling procedure to bring the liquid level in the manometer chamber and underwater seal chamber to the correct level and prevent overfilling or spilling of the liquid from one chamber to another.

SUMMARY OF THE INVENTION

In accordance with the present invention a filling device is provided for a pleural underwater drainage apparatus which permits the manometer chamber and underwater seal chamber to be separately filled through a rotatable funnel disposed in an opening at the upper end of the drainage apparatus.

In accordance with the invention an opening is provided at the upper end of the underwater drainage apparatus with approximately one-half of the opening disposed over the manometer chamber and the other half of the opening disposed over the underwater seal chamber. A rotatable funnel device is fitted into the opening and the funnel device is rotatable between a position wherein liquid may be poured into the manometer chamber while preventing liquid from entering the underwater seal chamber so as to fill the manometer chamber to the correct level and subsequently the funnel device may be rotated to fill the underwater seal chamber to the correct level while preventing water from entering the manometer chamber or vice versa. Thus, each chamber may be filled to the proper level without danger of overfilling due to liquid spilling over from one chamber to the other.

A removable cap is provided for the filling device which seals the opening and a positive pressure relief valve may be incorporated in the cap member. While positive pressure relief valves are known per se, as shown, for example, in U.S. Pat. No. RE 29,877. Such positive pressure relief valves are oneway valves which are set to exhaust to atmosphere from the underwater drainage apparatus when the positive pressure builds up within the drainage apparatus. Such a device prevents the collapse of a lung due to pressure buildup within the pleural cavity.

An object of the present invention is to provide a method and apparatus for prefilling an underwater drainage appartus.

Another object of the present invention is to provide a funnel which is rotatably mounted within an underwater drainage apparatus so as to permit liquid to be poured into the pressure manometer chamber and rotated to fill the underwater seal chamber to the desired level.

Still another object of the present invention is to provide a filling device and cap for an underwater drainage apparatus wherein an opening is provided in the top wall of an underwater drainage device disposed over the underwater seal chamber and manometer chamber with the funnel being rotatable to permit liquid to be poured into each chamber selectively and with a positive pressure relief valve disposed in the cap for the filling device.

Other objects and many of the attendant advantages of the present invention will become more readily apparent upon consideration of the following detailed specification in connection with the accompanying drawings wherein:

DETAILED DESCRIPTION OF THE PREFERRED EMBODIMENT

Figure 1:
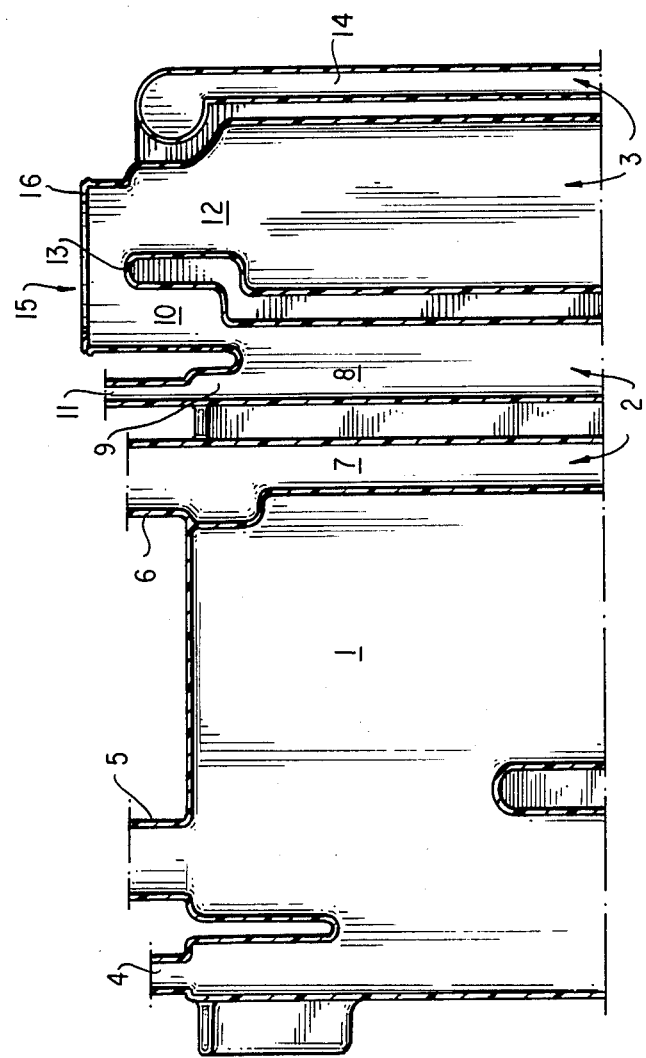
FIG. 1 is a cross sectional elevational view of an underwater drainage apparatus with which the filling device and cap of the present invention may be used.

Referring now more specifically to the drawings there is shown in FIG. 1 an elevational view in section of the upper end portion of an underwater drainage apparatus. The device may be made integrally and of plastic and includes three chambers, a collection chamber 1, an underwater seal chamber 2 and a pressure manometer chamber 3. The collection chamber 1 is provided with an opening 4 at the upper end thereof to which a thoracotomy tube may be attached. The distal end of the thoracotomy tube is inserted in the pleural cavity of a patient so that liquids and gas from the pleural cavity will flow through the thoracotomy tube and into the collection chamber 1. The upper end of the collection chamber 1 is provided with an outlet 5 which is connected through a passageway (not shown) with an inlet 6 into the upper end of the small arm 7 of the underwater seal chamber 2. The large arm 8 of the underwater seal chamber 2 has the lower end thereof in communication with the small arm 7 so as to form a U-tube as shown, for example, in U.S. Pat. No. 3,363,626. The upper end of the large arm 8 of underwater seal chamber 2 is divided into two passageways 9 and 10, passageway 9 leading to outlet 11 which may be connected to a suction source (not shown). Passageway 10 communicates with the large arm 12 of pressure manometer chamber 3 over the upper end of partition 13 which separates the large arm 8 of the underwater seal chamber 2 from the large arm 12 of the manometer chamber 3. The lower end of the large arm 12 of manometer chamber 3 communicates with the lower end of small arm 14 of the manometer chamber 3. The upper end 14 of the small arm of manometer chamber 3 is in communication with atmosphere. The manometer chamber 3 thus comprises a U-tube having a small and large arm similar to that shown in U.S. Pat. No. 3,363,626.

The upper end of the passageway 10 and large arm 12 of the manometer chamber 3 are formed with an opening 15 and the filling device of the present invention is disposed in this opening. The opening 15 is formed with an inwardly extending lip 16 as shown more clearly in FIG. 2.

Figure 2:
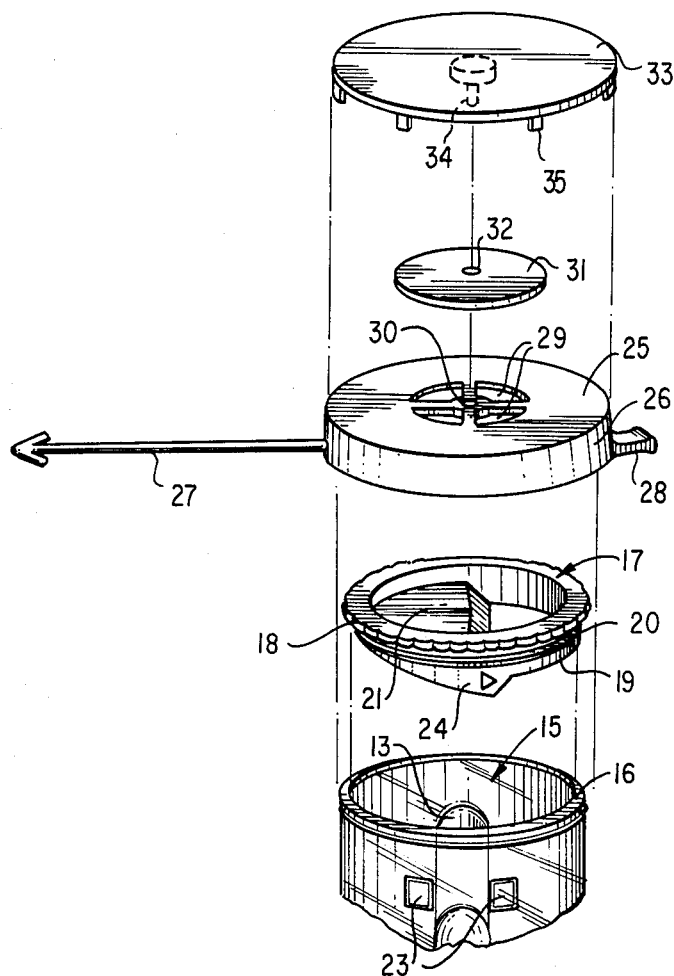
FIG. 2 is an exploded view of the filling device and cap of the present invention disposed over an opening in the upper end of an underwater seal chamber.
Figure 3:
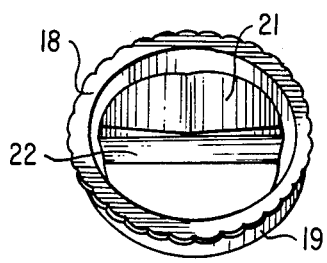
FIG. 3 is a perspective view of the funnel portion of the filling device.

A rotatable funnel 17 is shown in FIGS. 2 and 3 and the funnel is provided with a outwardly extending scalloped ring 18 and integrally formed downwardly extending flange 19. The flange 19 is provided with a circumferential groove 20 which is adapted to snap into engagement with the inwardly extending lip 16 of the opening 15. Thus, with the groove 20 engaging the lip 16 the funnel device 17 may be freely rotated by grasping the scalloped ring 18 and turning it with respect to the main body of the pleural drainage device.

Spaced below the scalloped ring 18 and integrally formed with the flange 19 is a funnelling device 21 which is shaped to direct liquids poured onto it towards the central portion of the opening. The funnelling device 21 has a lip 22 formed on the outer edge thereof. The funnelling device 21 and lip 22 cover approximately half of the opening 15 at the upper end of the drainage device.

Referring to FIG. 2 it can be seen that there are a pair of window outlines 23 marked on the housing of the drainage device surrounding the opening 15. The funnel 17 has a pair of downwardly extending tabs 24 spaced 180 degrees apart on the peripheral surface of flange 19. These tabs have arrows which cooperate with the window outlets 23 to show in which direction liquid will flow when poured into the filling device.

It can be seen that the partition 13 divides the opening 15 into approximately equal sized openings and that when the rotatable funnel is positioned as shown in FIG. 2 the liquid will flow into the large arm 12 of the pressure manometer chamber 13. When the scalloped ring 18 is rotated 180 degrees so that the arrow on the opposite side of the funnelling device 17 appears in the window outlet 23, liquid poured into the filling device will pass into the large arm 8 of the underwater seal chamber 2. The funnelling device 21 and lip 22 serve to prevent any liquid from spilling over into one chamber when the opposite chamber is being filled.

There is provided a cap for the funnelling device and this cap includes a cover plate 25 having a peripheral downwardly extending flange 26 with a tether 27 and hand grip 28 integrally moulded therewith. The outer end of the tether 27 may be affixed to the underwater drainage apparatus so as to prevent losing the cover during filling operations. The cover 25 has a plurality of openings 29 therein with a centrally located aperture 30. A flap valve 31 having a central opening 32 therein is disposed on the plate 25 so as to cover all of the openings 29. A cover member 33 has a central pin 34 affixed thereto which is adapted to pass through the opening 32 in flap valve 31 and be heat sealed within the opening 30. A plurality of depending tabs 35 are provided on the cover member 33 and these tabs engage the upper face of cap 25 to maintain the cover plate 33 in spaced relation with respect to the cap 25.

When the cap 25 is in place over the opening 15 and covering the filling device 17 the flap valve 31 normally covers the openings 29 in the cap 25 so that there is no outlet to atmosphere through the opening 15. However, in the event that the pressure within the drainage device is excessive the flap valve 31 will rise on the pin 34 within the space between the cap 25 and cover member 33. This will open the passageways 29 so that air can pass from within the drainage device through the openings 29 to atmosphere.

To fill the manometer chamber and seal chamber the cap 25 is grasped by the tab 28 and pulled upwardly off the circumferential wall surrounding the opening 15. The funnel device 17 is rotated so that the arrow on tab 24 appears within one of the window frames 23. When the tab is positioned as shown in FIG. 2 the funnel is arranged to deliver liquid to the manometer chamber 3. Water or other liquid may be poured into the funnel device 17 and the plate 2 and lip 22 will prevent water from passing into the underwater seal chamber 2. When the manometer chamber 3 is filled to the desired level the funnel device is rotated so that the arrow on the opposite side of the funnel 17 will appear within the other ring 23. In this position liquid will be delivered through the passageway 10 and into the large arm of the underwater seal chamber 2. In this way the underwater seal chamber and manometer chamber may be filled to the correct levels without overfilling or liquid spilling into the previously filled chamber.

Obviously many modificatins and variations of the present invention are possible in light of the above teachings.

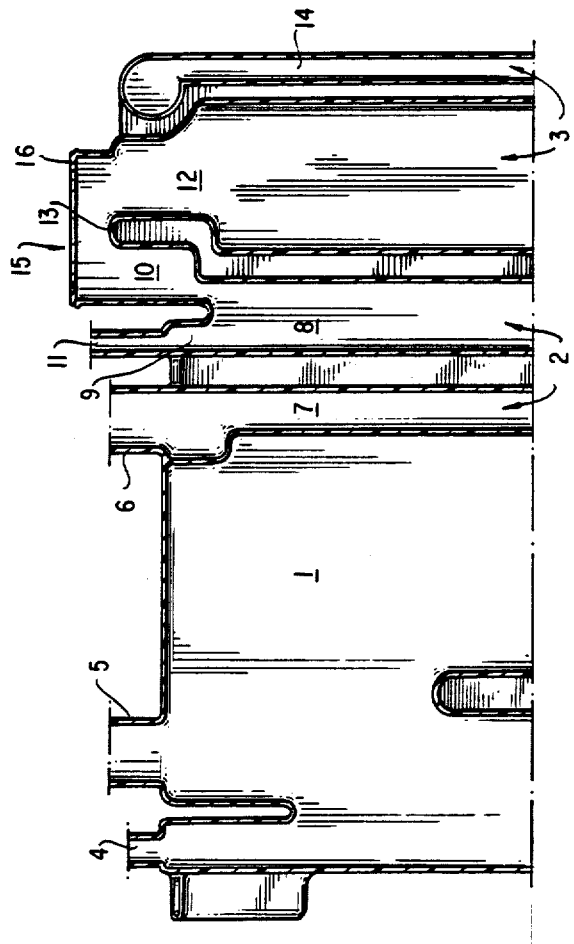

What is claimed as new and is desired to be secured by Letters Patent is:

1. A filling device for an underwater drainage device comprising a container with a manometer chamber, an underwater seal chamber and a collection chamber, a partition in said container between and separating the underwater seal chamber and the manometer chamber, a passageway formed within the drainage device disposed between the underwater seal chamber and the manometer chamber at the upper end of the partition, a common single opening formed by said passageway in the top wall of the container, said opening being enlarged so as to extend over both the manometer chamber and underwater seal chamber and in fluid communication with said passageway, and means disposed in said opening for selectively directing fluid into said underwater seal chamber or said manometer chamber.

2. A filling device for an underwater drainage device according to claim 1 wherein said means disposed in said opening includes a rotatable funnel in said opening in the top wall of said container and a removable cap in said rotatable funnel.

3. A filling device for an underwater drainage device according to claim 2 and further including a positive pressure relief valve in said cap.

4. A filling device for an underwater drainage device according to claim 3 wherein said cap includes a lower member having central openings therein, a flapper disc valve disposed over said openings and an upper member secured in spaced relation to said lower member.

5. A filling device for use on an underwater drainage device wherein the drainage device includes a container having a manometer chamber, an underwater seal chamber and a collection chamber with an opening in the top wall of the container, said opening extending partially over the manometer chamber and partially over the underwater seal chamber, said filling device including a funnel mounted in said opening, said funnel being rotatable to one position to direct fluid into the underwater seal chamber and to another position to direct fluid into the manometer chamber and a removable cap for said funnel.

6. A filling device according to claim 5 and further including a positive pressure relief valve in said removable cap.

7. A filling device according to claim 6 wherein said removable cap includes upper and lower spaced elements and a flaper valve disposed between said elements, said lower element having a peripheral flange thereon for press fitting around the rotatable funnel.

8. A method of preparing an underwater drainage device for use, the drainage device having a collection chamber, underwater seal chamber and manometer chamber with a rotatable funnel disposed in an opening in the top wall of the drainage device extending over the manometer chamber and the underwater seal chamber, comprising the steps of rotating the funnel to direct liquids into the underwater seal chamber, filling the underwater seal chamber to the desired level with liquid, rotating the funnel to direct liquid into the manometer chamber, filling the manometer chamber to the desired level with liquid, and placing a cap over the funnel to close the opening in the top wall of the drainage device.

* * * * *

UNITED STATES PATENT AND TRADEMARK OFFICE
CERTIFICATE OF CORRECTION

PATENT NO. : 4,723,949

DATED : Feb. 9, 1988

INVENTOR(S) : John S. Gentelia, et al

It is certified that error appears in the above-identified patent and that said Letters Patent is hereby corrected as shown below:

The title page should be deleted to appear as per attached title page.

Signed and Sealed this

Twelfth Day of July, 1988

*Attest:*

DONALD J. QUIGG

*Attesting Officer*   *Commissioner of Patents and Trademarks*

United States Patent

Gentelia et al.

[11] Patent Number: 4,723,949
[45] Date of Patent: Feb. 9, 1988

[54] FILLING DEVICE AND CAP FOR UNDERWATER DRAINAGE DEVICE

[75] Inventors: John S. Gentelia, Madison; Stephen J. Roberts, Sauquoit, both of N.Y.

[73] Assignee: ConMed, Inc., Utica, N.Y.

[21] Appl. No.: 906,957

[22] Filed: Sep. 15, 1986

[51] Int. Cl.⁴ ............................................. A61M 1/00
[52] U.S. Cl. ............................................... 604/321
[58] Field of Search .............. 137/205; 141/104, 248; 604/319–321, 119

[56] References Cited

U.S. PATENT DOCUMENTS 3,363,627  1/1968  Bidwell et al. ................. 604/321
4,354,493 10/1982  Kayser et al. ................. 604/321

FOREIGN PATENT DOCUMENTS 8403838 10/1984 PCT Int'l Appl. ............... 604/321

Primary Examiner—C. Fred Rosenbaum
Assistant Examiner—J. L. Kruter
Attorney, Agent, or Firm—Larson and Taylor

[57] ABSTRACT

A method and apparatus for filling an underwater drainage device is provided with a rotatable funnel and cap which is positioned between the manometer chamber and water seal chamber in a pleural drainage device. In use the cap may be removed and the funnel positioned to fill the manometer chamber to the desired level and the funnel may then be rotated to fill the underwater seal chamber to the desired level. A positive pressure relief valve is provided in the cap.

8 Claims, 3 Drawing Figures